United States Patent
McIntyre et al.

(10) Patent No.: US 11,654,286 B2
(45) Date of Patent: May 23, 2023

(54) OPTIMIZING DEEP BRAIN STIMULATION (DBS) PULSING BASED ON SYNAPTIC SUPPRESSION

(71) Applicant: Case Western Reserve University, Cleveland, OH (US)

(72) Inventors: Cameron McIntyre, Lakewood, OH (US); Amir Ali Farokhniaee, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 74 days.

(21) Appl. No.: 16/914,877

(22) Filed: Jun. 29, 2020

(65) Prior Publication Data

US 2021/0060345 A1 Mar. 4, 2021

Related U.S. Application Data

(60) Provisional application No. 62/893,399, filed on Aug. 29, 2019.

(51) Int. Cl.
*A61N 1/36* (2006.01)
*A61N 1/05* (2006.01)

(52) U.S. Cl.
CPC ....... *A61N 1/36171* (2013.01); *A61N 1/0534* (2013.01); *A61N 1/36139* (2013.01); *A61N 1/36175* (2013.01)

(58) Field of Classification Search
CPC .................................................... A61N 1/0534
See application file for complete search history.

(56) References Cited

U.S. PATENT DOCUMENTS

| | | | | |
|---|---|---|---|---|
| 2006/0074450 | A1* | 4/2006 | Boveja | A61N 1/36082 607/2 |
| 2012/0191157 | A1* | 7/2012 | Stypulkowski | A61N 1/0534 607/45 |
| 2013/0218232 | A1* | 8/2013 | Giftakis | A61N 1/3615 607/45 |

(Continued)

FOREIGN PATENT DOCUMENTS

AU 2015206540 B2 * 5/2017 ........... A61N 1/3605

OTHER PUBLICATIONS

Agnesi et al. "Fidelity of Frequency and Phase Entrainment of Circuit-Level Spike Activity During DBS." J Neurophysiol 114: 825-834, 2015, published on Jun. 18, 2015.

(Continued)

*Primary Examiner* — William J Levicky
(74) *Attorney, Agent, or Firm* — Eschweiler & Potashnik, LLC

(57) ABSTRACT

Embodiments discussed herein facilitate implementation of one or more DBS pulsing strategies that maximize synaptic suppression with the minimum number of stimuli. One example embodiment comprises a non-transitory computer-readable medium storing computer-executable instructions that, when executed, cause a processor to perform operations, comprising: applying deep brain stimulation (DBS) electrical stimulation according to a first mode to cause steady-state excitatory post-synaptic current (EPSC) suppression in a set of synapses; and applying DBS electrical stimulation according to a second mode that is different than the first mode to maintain EPSC suppression in the set of synapses.

27 Claims, 10 Drawing Sheets

(56) References Cited

U.S. PATENT DOCUMENTS

2016/0271413 A1* 9/2016 Vallejo ............... A61N 1/36062

OTHER PUBLICATIONS

Tass, Peter A. "A Model of Desynchronizing Deep Brain Stimulation With a Demand-Controlled Coordinated Reset of Neural Subpopulations." Biol. Cybern. 89, 81-88 (2003), published on Jul. 14, 2003.

* cited by examiner

OPTIMIZING DEEP BRAIN STIMULATION (DBS) PULSING BASED ON SYNAPTIC SUPPRESSION

CROSS REFERENCE TO RELATED APPLICATIONS

This application claims the benefit of U.S. Provisional Patent Application No. 62/893,399 filed Aug. 29, 2019, entitled "OPTIMIZING DEEP BRAIN STIMULATION (DBS) PULSING BASED ON SYNAPTIC SUPPRESSION", the contents of which are herein incorporated by reference in their entirety.

FEDERAL FUNDING NOTICE

This invention was made with government support under the grant(s) NS086100 awarded by the National Institutes of Health. The government has certain rights in the invention.

BACKGROUND

Deep brain stimulation (DBS) is a successful clinical therapy for a wide range of neurological disorders; however, the physiological mechanisms of DBS remain unresolved.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments discussed herein can comprise and/or employ techniques that can facilitate implementation of one or more DBS pulsing strategies that maximize synaptic suppression with the minimum number of stimuli and/or configuration of a DBS system to implement one or more such DBS pulsing strategies.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Figure 1:
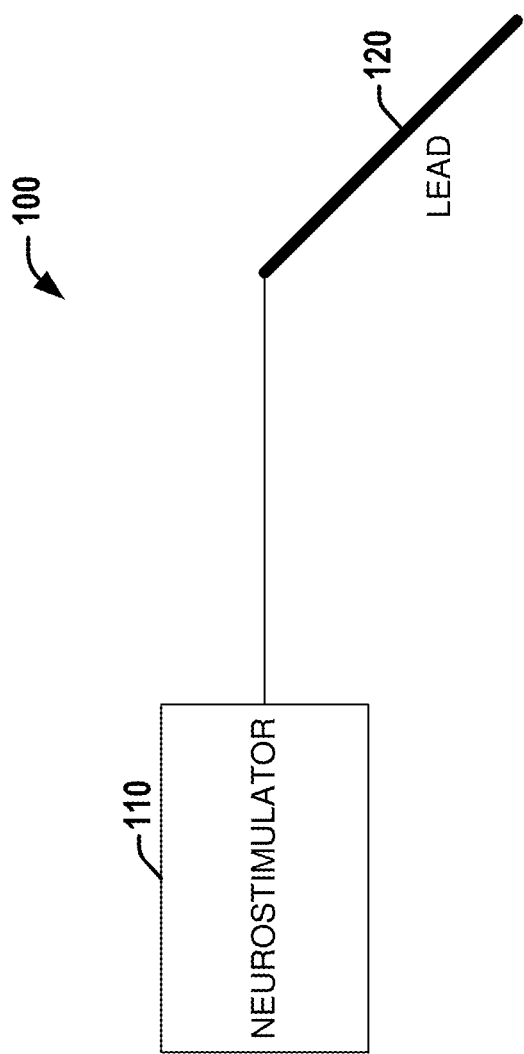
FIG. 1 illustrates an example deep brain stimulation (DBS) system that can facilitate maximized synaptic suppression with a minimum number of stimuli in connection with various embodiments discussed herein.

Referring to FIG. 1, illustrated is an example deep brain stimulation (DBS) system 100 that can facilitate maximized synaptic suppression with a minimum number of stimuli in connection with various embodiments discussed herein. DBS system 100 can comprise a neurostimulator (or implanted pulse generator, etc.) 110 and one or more leads 120. The components of DBS system 100 can be surgically implanted into a patient for treatment of any of a variety of conditions (e.g., Parkinson's disease, essential tremor, etc.), wherein lead(s) 120 can be implanted into a brain of a patient and configured to deliver electrical stimulation to a nucleus of the brain of the patient (e.g., the cerebellar-receiving area of thalamus (ventral posterolateral nucleus pars oralis (VPLo)), subthalamic nucleus (STN), globus pallidus (GP), etc.). Neurostimulator 110 can be implanted at another location in the patient's body (e.g., in the torso, etc.), and can be configured to generate the electrical stimulation delivered via lead(s) 120 (e.g., via a connecting wire that can be referred to as an extension, etc.). Neurostimulator 110 can be configured to communicate with one or more other devices, for example, a computer or other device for a managing physician to adjust one or more parameters associated with the electrical stimulation, a device to remotely activate or deactivate DBS system 100, etc.

In existing techniques, the electrical stimulation can be a tonic DBS electrical stimulation at a constant frequency. In various embodiments discussed herein, the electrical stimulation can be according to one of the DBS stimulation patterns discussed herein. In various embodiments, the DBS stimulation pattern can comprise a first mode that can cause affected synapses to enter steady-state excitatory post-synaptic current (EPSC) suppression, and a different second mode that maintain the fraction of neurotransmitter resources that remain available after synaptic transmission below a threshold near steady-state EPSC suppression. In various examples, the first mode can comprise a burst of high-frequency (e.g., above 100 Hz, such as around 130 Hz, e.g., between 120 Hz and 140 Hz, between 125 Hz and 135 Hz, 130 Hz, etc.) pulses (e.g., around 20 pulses at 130 Hz, or for around 150 ms, etc.). In some embodiments, the second mode can comprise a tonic electric stimulation at a lower frequency than the first mode (e.g., approximately every 10.5 or 10-11 ms, e.g., around 95 Hz (e.g., 90-100 Hz, 93-97 Hz, 95 Hz, etc.), etc.). In other embodiments, the second mode can comprise operating at the high frequency according to a reduced duty cycle comprising a repeating pattern of DBS pulses during a run time followed by inactivity during a pause time.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
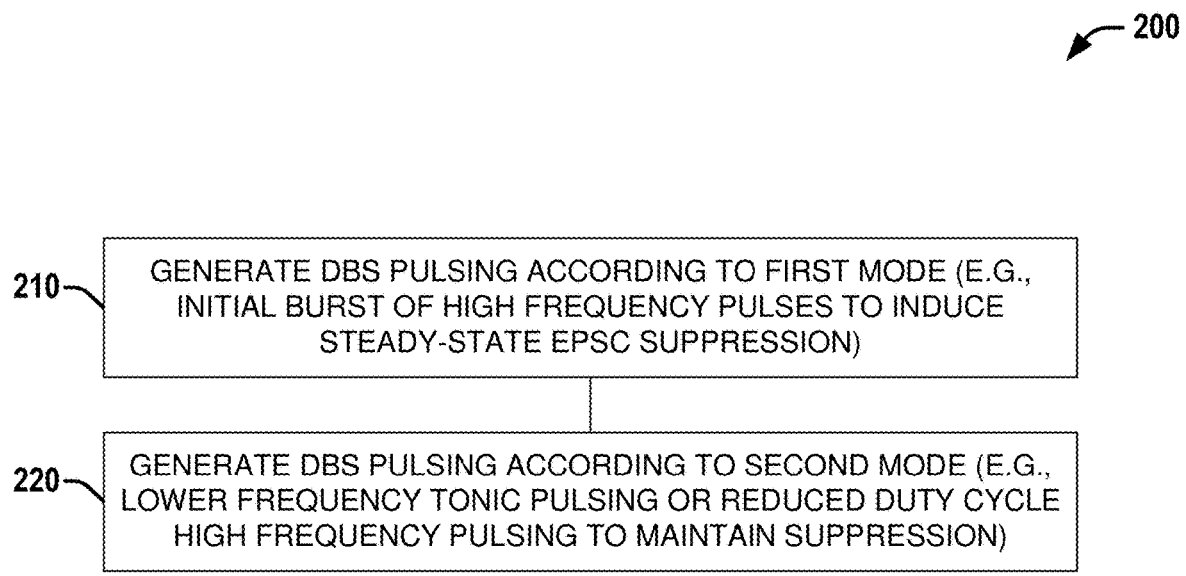
FIG. 2 illustrates a flow diagram of an example method/set of operations employable at a DBS system that facilitates maximized synaptic suppression with a minimum number of stimuli, according to various embodiments discussed herein.

Referring to FIG. 2, illustrated is a flow diagram of an example method or process 200 employable at a DBS system that facilitates maximized synaptic suppression with a minimum number of stimuli, according to various embodiments discussed herein. In other aspects, a machine readable medium can store instructions associated with method 200 that, when executed, can cause a DBS system to perform the acts of method 200.

At 210, DBS pulsing can be generated according to a first mode to induce steady-state EPSC suppression. In various embodiments, the first mode can comprise an initial burst of high frequency (e.g., around 130 Hz) pulses to quickly push affected synapses into steady-state EPSC suppression.

At 220, DBS pulsing can be generated according to a second mode that is different than the first mode to maintain EPSC suppression. In various embodiments, the second mode can comprise one of tonic stimuli at a lower frequency than the first mode (e.g., around 95 Hz, etc.) or repeated alternation between pulsing at the frequency of the first mode and inactivity according to a run time and a pause time, respectively, as discussed in greater detail herein. In some embodiments, DBS pulse activation in the second mode can depend on a threshold for the fraction of neurotransmitter resources that remain available after synaptic transmission below a threshold near steady-state EPSC suppression, wherein the nature of the second mode (e.g., tonic stimuli or alternating between pulsing and inactivity) can depend on the specific threshold.

Additionally or alternatively, method 200 can include one or more other acts described herein in connection with various aspects and/or embodiments.

Additional aspects and embodiments are discussed below in connection with the following example use case.

Example Use Case: Theoretical Principles of Deep Brain Stimulation (DBS) Induced Synaptic Suppression and Associated DBS Pulsing Techniques The following discussion provides example embodiments in connection with an example use case involving DBS pulsing techniques that can maximize synaptic suppression with a minimum number of stimuli.

1. Overview

Deep brain stimulation (DBS) is a successful clinical therapy for a wide range of neurological disorders; however, the physiological mechanisms of DBS remain unresolved. While many different hypotheses currently exist, analyses associated with the example use case suggest that high frequency (~100 Hz) stimulation-induced synaptic suppression represents the most basic concept that can be directly reconciled with experimental recordings of spiking activity in neurons that are being driven by DBS inputs. The example use case developed a simple model system to characterize the excitatory post-synaptic currents (EPSCs) and action potential signaling generated in a neuron that is strongly connected to pre-synaptic glutamatergic inputs that are being directly activated by DBS. The Tsodyks-Markram (TM) phenomenological synapse model was used to represent depressing, facilitating, and pseudo-linear synapses driven by DBS over a wide range of stimulation frequencies. The EPSCs were then used as inputs to a leaky integrate-and-fire neuron model and measured the DBS-triggered post-synaptic spiking activity was measured. Synaptic suppression was a robust feature of high frequency stimulation, independent of the synapse type. As such, the TM equations were used to define alternative DBS pulsing strategies that maximize synaptic suppression with the minimum number of stimuli. As shown by the example use case, synaptic suppression provides a biophysical explanation to the intermittent, but still time-locked, post-synaptic firing characteristics commonly seen in DBS experimental recordings. Therefore, network models attempting to analyze or predict the effects of DBS on neural activity patterns should integrate synaptic suppression into their simulations.

2. Introduction

The most common approach to modulate the nervous system with electrical stimulation is to use a brief stimulus pulse (~100 μs) to generate an extracellular electric field. This electric field manipulates the voltage sensor of sodium ion channels embedded in the membrane of neurons into generating a propagating action potential (AP). The basic point and purpose of generating the AP is have it invade the synaptic terminals of the neuron and subsequently control the release of neurotransmitters with the explicit timing of the electrical. However, the release of neurotransmitters from a synapse, as well as the resulting post-synaptic currents (PSCs), are dependent upon the firing history of the synapse. Given that clinical stimulation technologies typically rely on a constant stimulation frequency, a key parameter of interest is the steady-state PSC generated at the synapse as a function of the stimulation frequency. In general, low stimulation frequencies (~10 Hz) can maintain high levels of PSCs over prolonged periods of time; however, high stimulation frequencies (~100 Hz) typically suppress PSCs quickly after the onset of the stimulus train.

The concept of high frequency stimulation-induced suppression of synaptic transmission can be especially relevant to the therapeutic mechanisms of deep brain stimulation (DBS). The development of ~100 Hz DBS therapies have traditionally followed from the clinical foundation of ablative therapies performed within the same brain circuits. In addition, the neurological disorders associated with successful DBS interventions are typically characterized by abnormal oscillatory activity within the afflicted brain networks. As such, stimulation-induced suppression of synaptic communication in the directly activated neurons is consistent with the general effect of ablation on neural activity, as well as the disruption of oscillatory signal transmission through a network.

Most in vivo experimental measures of DBS do not show a complete cessation of communication between the directly stimulated pre-synaptic neuron and a strongly connected post-synaptic neuron. Instead, signal transmission that under low frequency stimulation is robust, becomes intermittent and low fidelity during high frequency stimulation, albeit still time-locked to the stimulus train. This suggests that DBS alters the dynamics of these synaptic connections, which may act as a filter on the inputs from the pre-synaptic neuron that are able to influence the post-synaptic neuron.

Detailed biophysical models of DBS have consistently shown robust AP initiation and propagation to ~100 Hz stimuli with ~100% fidelity in neurons that are in close proximity (~1 mm) to the stimulating electrode. In addition, extensive axonal conduction parameter sensitivity studies suggest that DBS-induced APs are able to propagate to their axon terminals with a very high safety margin. Therefore, while difficult to document experimentally, strong theoretical evidence supports the assumption of robust and high-fidelity AP invasion of the pre-synaptic terminals of directly stimulated neurons during DBS. If APs invade a synaptic bouton at high frequencies for long periods of time, the available experimental evidence clearly shows a marked suppression in the post-synaptic currents.

The general phenomenon of DBS-induced synaptic suppression can be most easily studied at glutamatergic synapses, where a wealth of experimental data exists to parameterize synaptic models, and APs time-locked to the stimuli can be monitored in post-synaptic neurons. However, quantitative details on the specific effects of sustained high frequency synaptic driving are lacking in both the computational and experimental literature. In addition, multiple types of glutamatergic synapses are known to exist, including depressing, facilitating, and pseudo-linear. The example use case quantified how these different synapse types respond to DBS, and then used a leaky integrate-and-fire (LIF) neuron model to evaluate the post-synaptic effects on action potential signaling. Based on this relatively simple model rooted in synaptic fundamentals, an analytical optimization of DBS pulsing was developed to maximize synaptic suppression with the minimum number of stimuli.

3. Methods

The example use case developed a simple model system to characterize the excitatory post-synaptic currents (EPSCs) and action potential (AP) signaling generated in a neuron that is strongly connected to pre-synaptic glutamatergic inputs that are being directly activated by deep brain stimulation (DBS). The Tsodyks-Markram (TM) phenomenological synapse model was used to represent depressing (D), facilitating (F), and pseudo-linear (P) glutamatergic synapses driven by DBS over a wide range of stimulation frequencies. The post-synaptic EPSCs predicted by the DBS-driven TM synapses were then used as inputs to a leaky integrate-and-fire (LIF) neuron model that exhibited a stochastic background firing rate of ~20 Hz. The neuronal output of interest was the DBS-triggered post-synaptic spiking activity in the LIF neuron as a function of the DBS frequency.

Experimental Example

Figure 3:
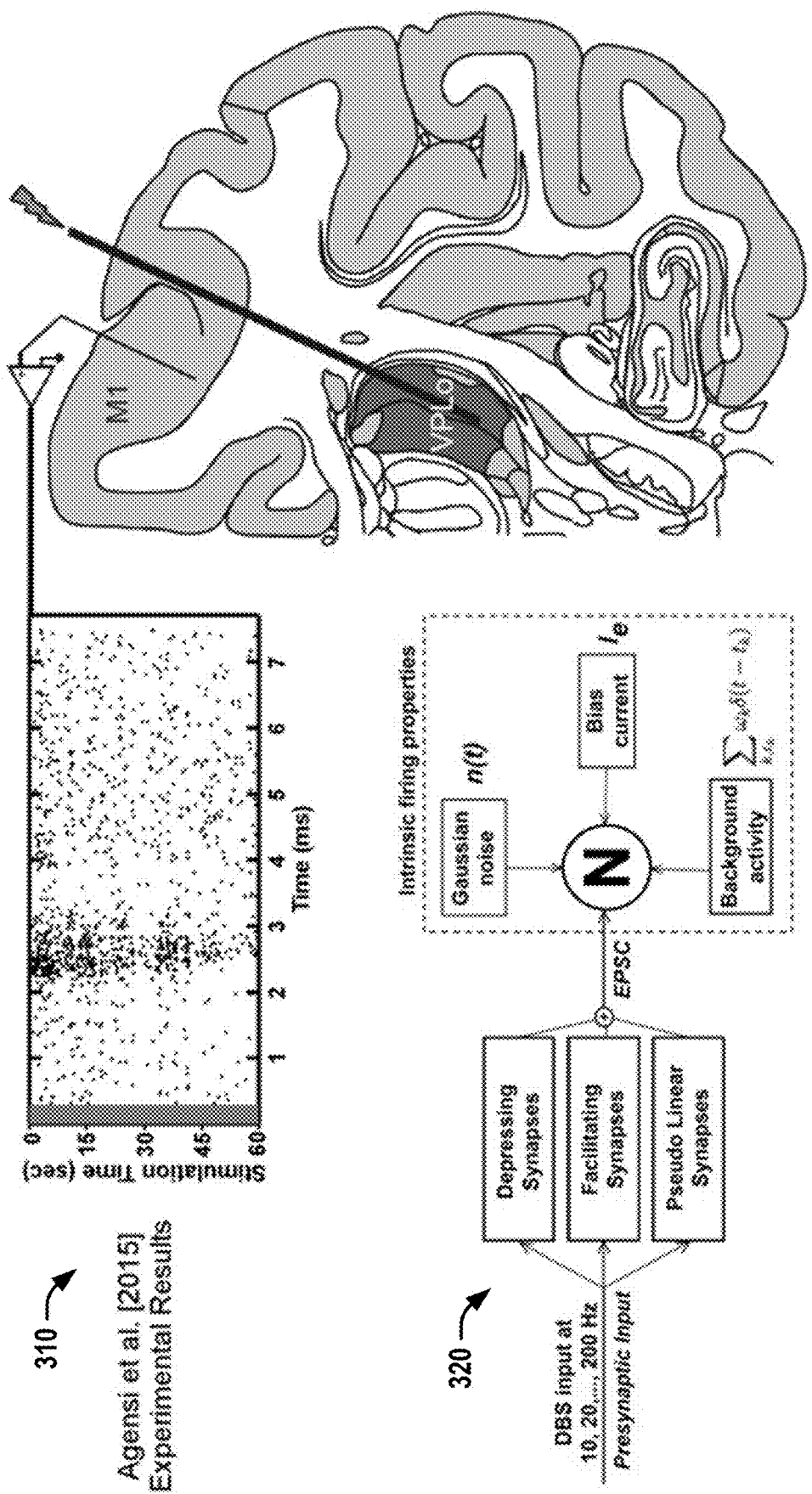
FIG. 3 illustrates a diagram showing experimental results for stimulus-triggered action potentials during deep brain stimulation and a model of DBS synaptic modulation of a neuron (N) with intrinsic firing, in connection with various aspects discussed herein.

One motivation for developing this DBS model system was to provide a biophysical explanation for the complex experimental peri-stimulus time histograms typically recorded from individual neurons that are being modulated by DBS-driven glutamatergic synaptic inputs. Referring to FIG. 3, illustrated is a diagram showing experimental results for stimulus-triggered action potentials during deep brain stimulation and a model of DBS synaptic modulation of a neuron (N) with intrinsic firing, in connection with various aspects discussed herein. FIG. 3 provides an example of the general concepts of interest, explicitly illustrating results from the work of Agensi et al. at 310. In those experiments, DBS was applied in the thalamus (VPLo) and coupled with simultaneous single unit recordings in the cortex (M1). The experiments observed time-locked spiking activity in M1 neurons during DBS and plotted the stimulus-triggered APs as stacked raster plots over each interstimulus interval (~8 ms) for 1 min of 130 Hz thalamic DBS (7,800 total pulses), as shown in the plot at 310. The example neuron shown in FIG. 3 was driven by a strong monosynaptic glutamatergic connection from directly activated neural elements in thalamus. However, during high frequency DBS, those experiments found that the entrainment patterns of cells in M1 never followed a one-to-one pattern of each stimulus pulse eliciting a unit-spike response in M1. Instead, the M1 neurons exhibited intermittent AP responses to the DBS-driven synaptic input, which tended to decrease in fidelity over time. These general DBS entrainment patterns are common for in vivo recordings of neurons that are being modulated by DBS-driven glutamatergic synaptic inputs. Unfortunately, the biophysical mechanisms responsible for these experimental observations are only loosely defined, and computational models attempting to simulate neural network activity induced by DBS have historically ignored them. Therefore, one goal of the example use case was to create a simple modeling infrastructure that can better account for the physiological realities of in vivo synaptic integration during DBS.

Synapse Model

The example use case used the Tsodyks-Markram (TM) phenomenological model of short-term synaptic plasticity to quantify the dynamic behavior of glutamatergic synapses being driven by DBS-induced action potentials. TM models have the ability to simulate both short-term depression (associated with the depletion of neurotransmitter) and short-term facilitation (associated with the influx of calcium into the pre-synaptic terminal). The dynamics of the TM model arise from the combination of a depression effect, denoted by normalized variable x, which represents the fraction of neurotransmitter resources that remain available after synaptic transmission, and a facilitation effect modeled by utilization parameter u that represents the fraction of available neurotransmitter resources ready to be used. As such, u is consumed to produce the postsynaptic current, I. The combination of the depression and facilitation effects, as well as the time delay, Δ, yields the differential equations of equations (1)-(3):

$$\dot{u} = -\frac{u}{\tau_f} + U(1-u^-)\delta(t-t_s-\Delta) \quad (1)$$

$$\dot{x} = -\frac{1-x}{\tau_d} - u^+x^-\delta(t-t_s-\Delta) \quad (2)$$

$$\dot{I} = -\frac{I}{\tau_s} + Au^+x^-\delta(t-t_s-\Delta) \quad (3)$$

where $t_s$ is the spike time, δ is the Dirac delta function, U is the increment of u produced by an incoming spike, $\tau_f$ is the decay time constant of variable u, $\tau_d$ is the recovery time constant of variable x, $\tau_s$ is the decay time constant of variable I, and A denotes the synaptic response amplitude that would be produced with the release of all neurotransmitters (absolute synaptic response). The specific parameter values for the D, F, and P synapses are listed in Table 1, which were defined to match the experimentally measured characteristics of intracortical glutamatergic EPSCs.

TABLE 1

Parameter Values for F, D, and P synapses

| Synapse | $\tau_f$ (ms) | $\tau_d$ (ms) | $\tau_s$ (ms) | U | A (μA) |
|---|---|---|---|---|---|
| F | 670 | 138 | 3 | 0.09 | 2.5 |
| D | 17 | 671 | 3 | 0.5 | 2.5 |
| P | 326 | 329 | 3 | 0.29 | 2.5 |

Post-Synaptic Neuron Model

The example use case used a noisy leaky-integrate-and-fire (LIF) neuron model to evaluate the post-synaptic response to the DBS-driven synaptic inputs, as shown at 320. The LIF neuron was parameterized to exhibit an intrinsic tonic firing pattern at ~20 Hz. This was achieved by incorporating a bias current, $I_e$ (0.56 nA), background synaptic inputs that arrived stochastically at $t_k$ via a Poissonian process with rate $\omega_k$, and white Gaussian noise, n(t). The noise had a mean of 0 and variance ($\sigma^2$) of 0, 2.5, and 5 for examples of no noise, default noise, and high noise simulations, respectively. The LIF neuron also received glutamatergic inputs from DBS-driven synapses, where TM models simulated EPSCs that could also be modulated by a synaptic fidelity coefficient ($\omega_{sf}$). Therefore, the transmembrane potential, v, of the LIF neuron model was defined by the differential equation of equation (4):

$$C_m\dot{v} = \frac{E_l - v}{R_m} + I_e + \omega_{sf}EPSC\sum_{k,t_k}\omega_k\delta(t-t_k) + n(t) \quad (4)$$

where $C_m$ (1 μF) and $R_m$ (100 MΩ) are the membrane capacitance and resistance respectively, and $E_l$ (−70 mV) is the leak voltage. The simulations were performed in MATLAB.

4. Results

Synaptic Response to DBS

Figure 4:
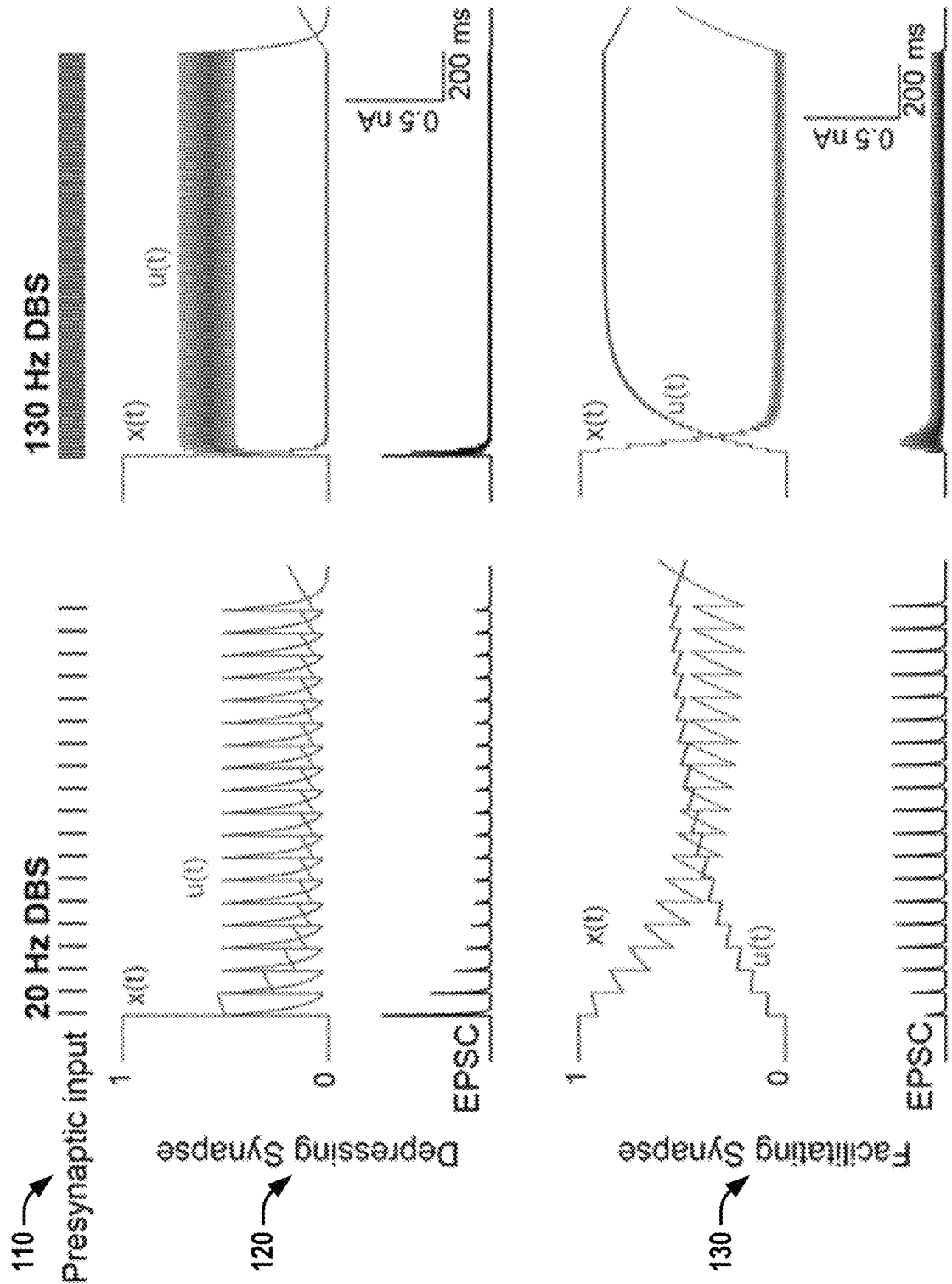
FIG. 4 illustrates a series of diagrams showing Tsodyks-Markram (TM) synapse model responses for facilitating and depressing synapses to two different presynaptic inputs, in connection with various aspects discussed herein.
Figure 5:
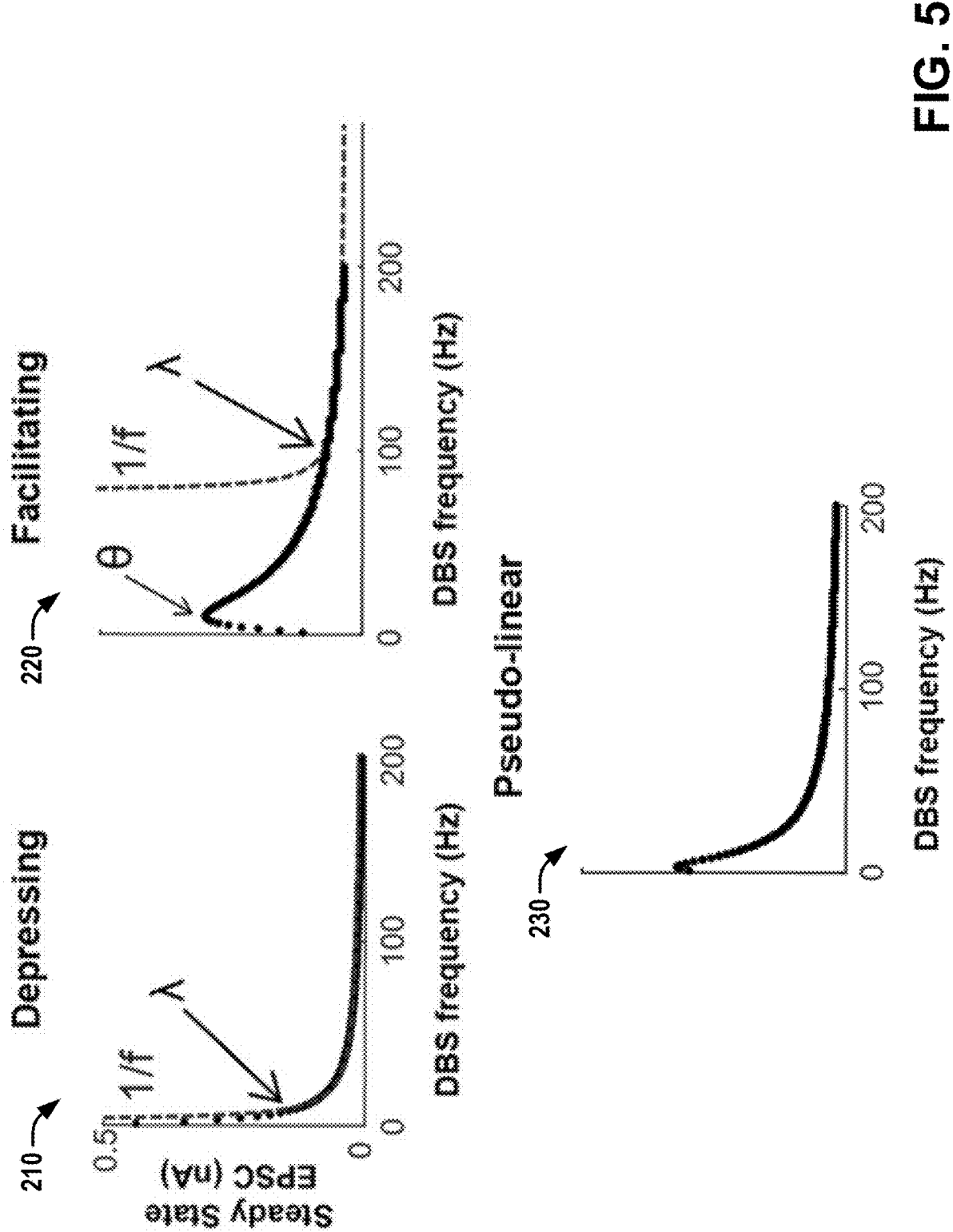
FIG. 5 illustrates synaptic gain diagrams for depressing, facilitating, and pseudo-linear synapses, showing the steady-state EPSC amplitude as a function of DBS frequency, in connection with various aspects discussed herein.

Simulations of the TM synaptic model demonstrate that low frequency stimulation can generate a wide range of EPSCs that depend upon the type of synapse (e.g., P, D, or F), as well as the timing of when the EPSC is being evaluated during the stimulus train (e.g., onset or steady-state). Referring to FIG. 4, illustrated is a series of diagrams showing TM synapse model responses for facilitating and depressing synapses to two different presynaptic inputs, in connection with various aspects discussed herein. At 410 are shown two different example DBS pulses, 20 Hz for 1 second (left column) and 130 Hz for 1 second (right column), as example presynaptic inputs. For a D synapse driven at 20 Hz, the number of available resources for transmission, x(t), decay with a fast time constant. This results in EPSCs that are initially very strong, but depress to a moderate amplitude in the steady-state, as seen in the left column of 420. On the other hand, F synapses driven at 20 Hz exhibit an x(t) that does not decay quickly because the usage fractions, u(t), are smaller. This results in EPSCs that are initially moderate in size, but increase over time to become higher amplitude in the steady-state, as seen in the left column of 430. However, both the F and D synapses exhibit a similar trend of steady-state EPSC suppression under high frequency driving, as seen in the right column of 420 and 430. F synapses depress to small EPSC amplitudes and D synapse EPSCs reduce to nearly zero during 130 Hz driving. Referring to FIG. 5, illustrated are synaptic gain diagrams for depressing (510), facilitating (520), and pseudo-linear (530) synapses, showing the steady-state EPSC amplitude as a function of DBS frequency, in connection with various aspects discussed herein. In FIG. 5, λ is the limiting frequency, and 8 is the peak frequency. FIG. 5 provides the steady-state amplitude of the post-synaptic response as a function of the DBS frequency in 1 Hz increments. As can be seen in FIG. 5, independent of the synapse type (D, F, P), high frequency driving of the synapse models generates marked EPSC suppression.

When an F synapse gets stimulated at progressively increasing DBS frequencies, the steady-state EPSC amplitude initially increases at lower frequencies and then decreases at higher frequencies, which produces a bell-shaped curve, as seen at 520. The peak of the gain function is called the "peak frequency," which has a theoretical value given by equation (5):

$$\theta = \frac{1}{\sqrt{U\cdot\tau_f\cdot\tau_d}} \quad (5)$$

For both F and D synapses, the gain diagrams decrease in 1/f fashion, where f is the stimulation frequency. This characteristic is called the "limiting frequency," λ, as seen in 510 and 520. Experimental measurements of λ range from 70-130 Hz for F synapses, and 5-30 Hz for D synapses. The specific TM synapse model parameterizations of the example use case (in Table 1) result in a λ of 11 Hz for the D synapse and 100 Hz for the F synapse. Pseudo-linear synapses represent a combination of F and D behavior, but nonetheless also exhibits EPSC suppression at high stimulation frequencies.

Post-Synaptic Neuron Firing

Figure 6:
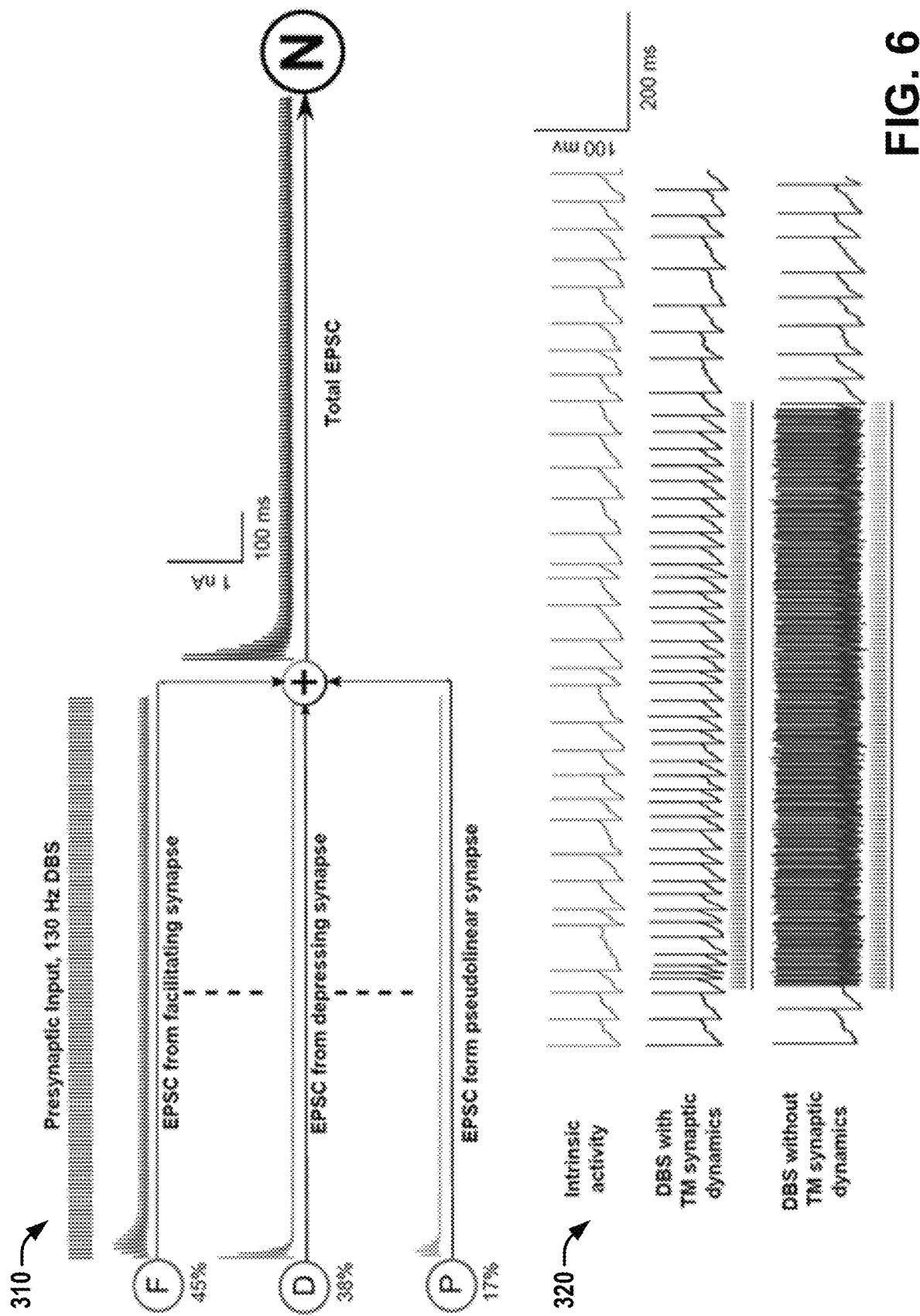
FIG. 6 illustrates a diagram showing DBS driven synaptic modulation of a leaky-integrate-and-fire (LIF) neuron model, in connection with various aspects discussed herein.

Given the EPSC modulation at individual synapses by DBS inputs (e.g., as shown in FIG. 5), the total EPSC for many synapses converging on an individual post-synaptic neuron will also be modulated. To simulate this phenomenon a LIF neuron model was created for the example use case that received a total of 100 glutamatergic synaptic inputs, which were explicitly driven by the DBS signal (with a 2 ms AP transmission delay from thalamus). The various synaptic inputs were designated as F (45), D (38), or P (17) based on physiologically relevant distributions of the synapse types. When a single DBS pulse was initiated in these synaptic inputs, the EPSCs were generated simultaneously in the LIF neuron, thereby creating a total DBS EPSC that was a mix of F, D, and P components. Referring to FIG. 6, illustrated is a diagram showing DBS driven synaptic modulation of a leaky-integrate-and-fire (LIF) neuron model, in connection with various aspects discussed herein. At 610 is shown 100 different synaptic inputs, driven by the DBS signal, to the LIF neuron model N, where the distribution of F, D, and P synapse types is based on experimental estimates. At 620 is shown the response of N when driven by DBS inputs with or without TM synaptic dynamics. A single DBS EPSC, generated with the initial conditions of the synapse models, was a suprathreshold for the generation of a stimulus evoked AP in the LIF neuron. High frequency driving (130 Hz) of the DBS synaptic input generated an initial burst of APs in the LIF neuron and then as the total DBS EPSC reduced in amplitude to a steady-state value, the inputs provided sub-threshold excitatory inputs to the LIF neuron, as seen at 620. The overall result of this DBS-driven excitatory bias current was an increased average firing rate, but AP firing in the LIF neuron remained stochastic, albeit commonly time locked to a DBS input pulse.

Figure 7:
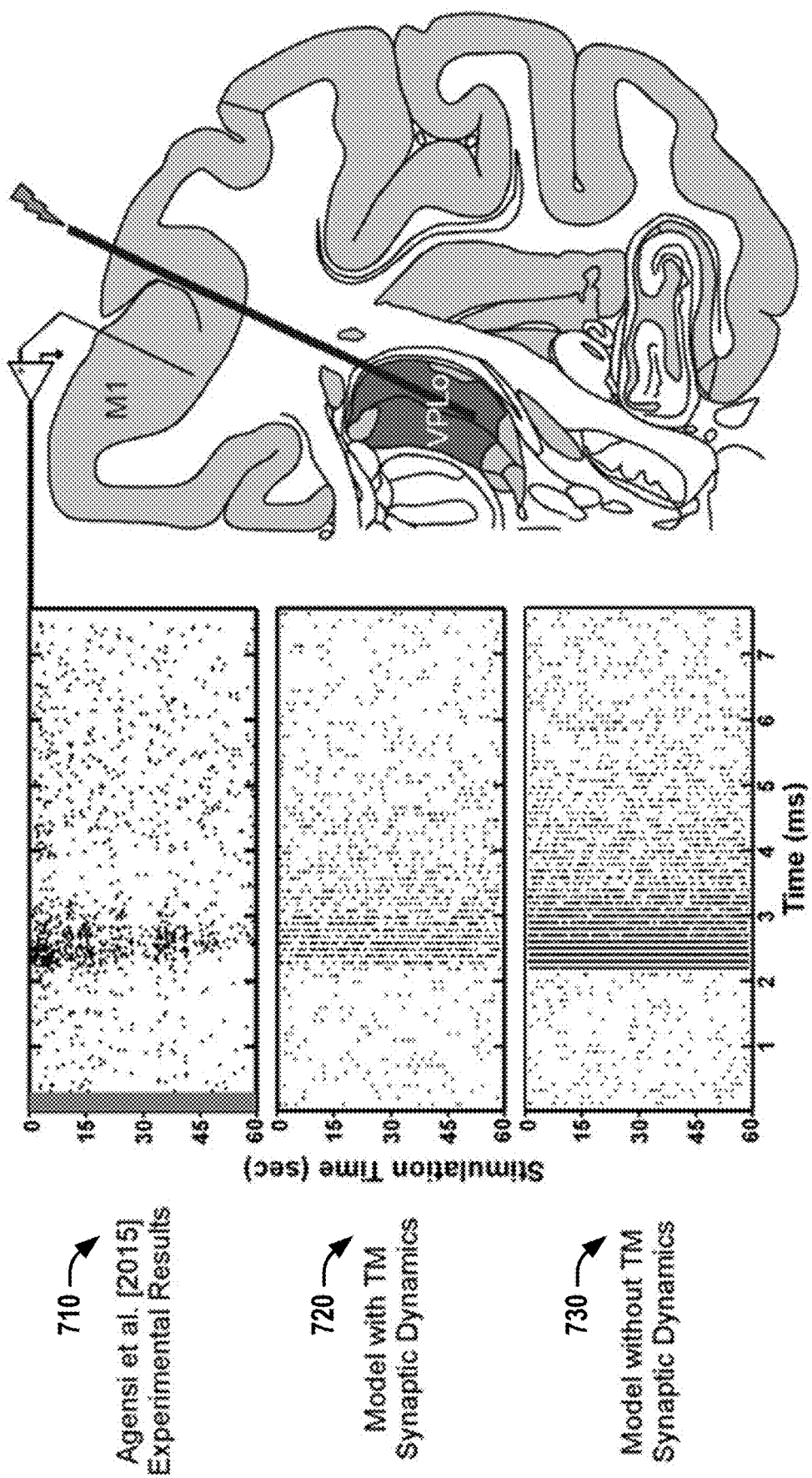
FIG. 7 illustrates raster plots showing a comparison between experimental results of stimulus-triggered action potentials (APs) in M1 during thalamic DBS with the LIF neuron model with TM synaptic dynamics and without TM synaptic dynamics, in connection with various aspects discussed herein.

Referring to FIG. 7, illustrated are raster plots showing a comparison between experimental results of stimulus-triggered APs in M1 during thalamic DBS (at 710) with the LIF neuron model with TM synaptic dynamics (at 720) and without TM synaptic dynamics (at 730), in connection with various aspects discussed herein. The general firing characteristics achieved with TM synaptic dynamics are consistent with experimental recordings of post-synaptic glutamatergic modulation by DBS-driven inputs, as seen by comparing 710 and 720. Alternatively, if the DBS EPSC is simply maintained at its initial conditions indefinitely, as done in nearly every DBS network model ever created, the response in the LIF neuron was a dramatic increase in firing that is not representative of typical experimental recordings, as seen at 620 (the bottom graph) and by comparing 710 and 720. Nonetheless, short-term synaptic suppression alone does not explain all of the features noted in experimental results. Other factors, such as spike timing dependent plasticity, are also likely to be responsible for the continued decay in synaptic fidelity over the course of 1 min of continuous DBS, as discussed in greater detail below.

Optimization of DBS Pulsing

The majority of neurons with DBS-driven synaptic inputs are unlikely to be so strongly connected to those inputs that a single DBS-driven EPSC would be capable of generating an AP. As such, the primary effect of suppressing the steady-state EPSC on these more weakly connected neurons would be to minimize any synaptic influence from those DBS-driven connections. This follows the general hypothesis that a basic mechanism of high frequency DBS is the effective disconnection of directly stimulated neurons from their underlying brain networks via synaptic suppression.

Figure 8:
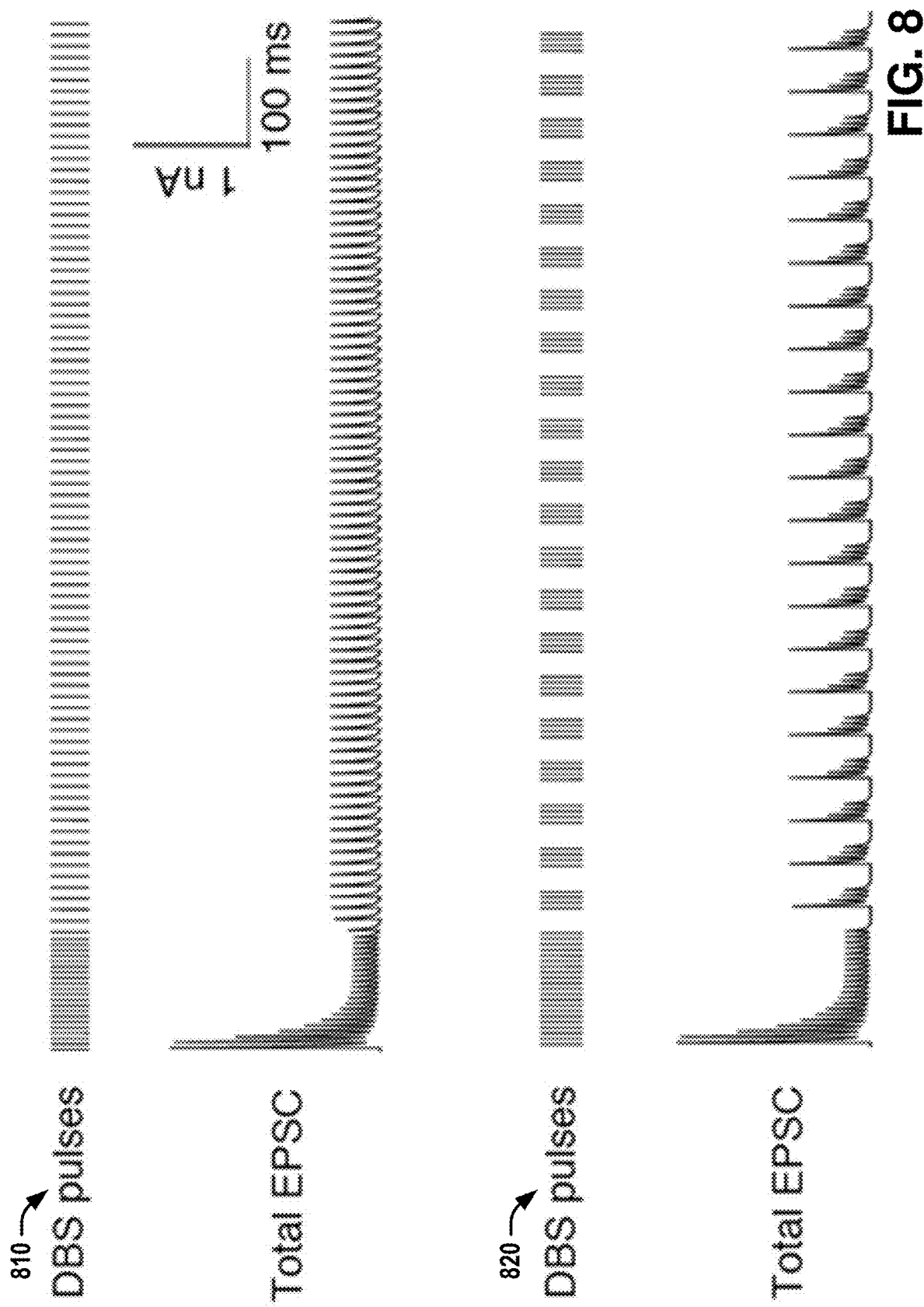
FIG. 8 illustrates example DBS pulsing strategies that can maximize suppression with minimized inputs, in connection with various aspects discussed herein.

Given the hypothesized goal of DBS-driven synaptic disconnection, the TM equations were used to design stimulation paradigms that could similarly achieve the synaptic suppression observed with traditional tonic DBS, but with fewer stimuli. The key parameters for consideration are u (equation (1)) and x (equation (2)), where the goal is to minimize x and maximize u across the various synapse types that connect to the post-synaptic neuron, as shown in FIG. 4. Referring to FIG. 8, illustrated are example DBS pulsing strategies that can maximize suppression with minimized inputs, in connection with various aspects discussed herein.

At 810 is an example of a first DBS pulsing strategy employable by various embodiments, which uses an initial burst of high frequency pulses to quickly push the system into the steady-state regime (FIG. 5), and then maintains the suppressed EPSCs by pulsing the system at a somewhat lower tonic frequency. An analytical optimization of this tonic stimulation concept using the TM equations is discussed below. Example 810 demonstrates this DBS paradigm using 20 pulses at 130 Hz for the initial burst, followed by tonic stimuli every 10.5 ms (~95 Hz), using the overall model system as parameterized in FIG. 6. The first DBS pulsing strategy employs high frequency pulses until the parameter x reaches steady state, followed by pulsing at a tonic frequency lower than the high frequency pulses. Although 810 is provided as one example of the first DBS pulsing strategy, in various embodiments, DBS pulsing according to the first pulsing strategy can be employed that can vary from example 810 (e.g., with one or more of a different initial high frequency, a different duration of the initial high frequency, or a different tonic frequency, etc.).

A different optimization strategy employable as a DBS pulsing strategy by various embodiments is to follow an initial burst of DBS pulses with subsequent bursts of DBS pulses delivered on a reduced duty cycle. Once again, the concept is to suppress the E PSCs at stimulation onset with a large burst, and then use smaller bursts to maintain the synaptic suppression. An analytical optimization of this burst stimulation concept using the TM equations is also discussed below. At 820 is an example of this DBS paradigm using 20 pulses at 130 Hz for the initial burst, followed by bursts with 4 pulses at 130 Hz delivered every 37 ms (~50% duty cycle), using the overall model system as parameterized in FIG. 6. The second DBS pulsing strategy employs high frequency pulses until the parameter x reaches steady state, followed by subsequent DBS pulsing at a reduced duty cycle. Although 820 is provided as one example of the first DBS pulsing strategy, in various embodiments, DBS pulsing according to the second pulsing strategy can be employed that can vary from example 820 (e.g., with one or more of a different initial high frequency, a different duration of the initial high frequency, or a different tonic frequency, etc.).

In various embodiments, the alternative stimulation paradigms discussed herein (e.g., the first and/or second DBS pulsing strategy discussed above) can be further optimized for clinical effect based upon quantitative details associated with the specific axonal pathway(s) that are being directly modulated by DBS and the specific synapse types associated with those connections. In some embodiments, some of these quantitative details can depend on details that can be common to multiple patients, and some can depend on details that can vary between patients (e.g., lead placement, etc.). As such, while the examples in FIG. 8 provide a demonstration of the concept of synaptic suppression based DBS optimization, and in some embodiments, they can be employed as DBS pulsing techniques, in other embodiments, they can be employed as a starting point for further optimization (e.g., including patient-specific, etc.). Even without further optimization, however, the alternative DBS paradigms discussed herein show promise for reducing the total number of DBS pulses necessary to achieve a hypothesized neurophysiological mechanism of action.

5. Analytical Optimization of DBS Pulsing

Figure 9:
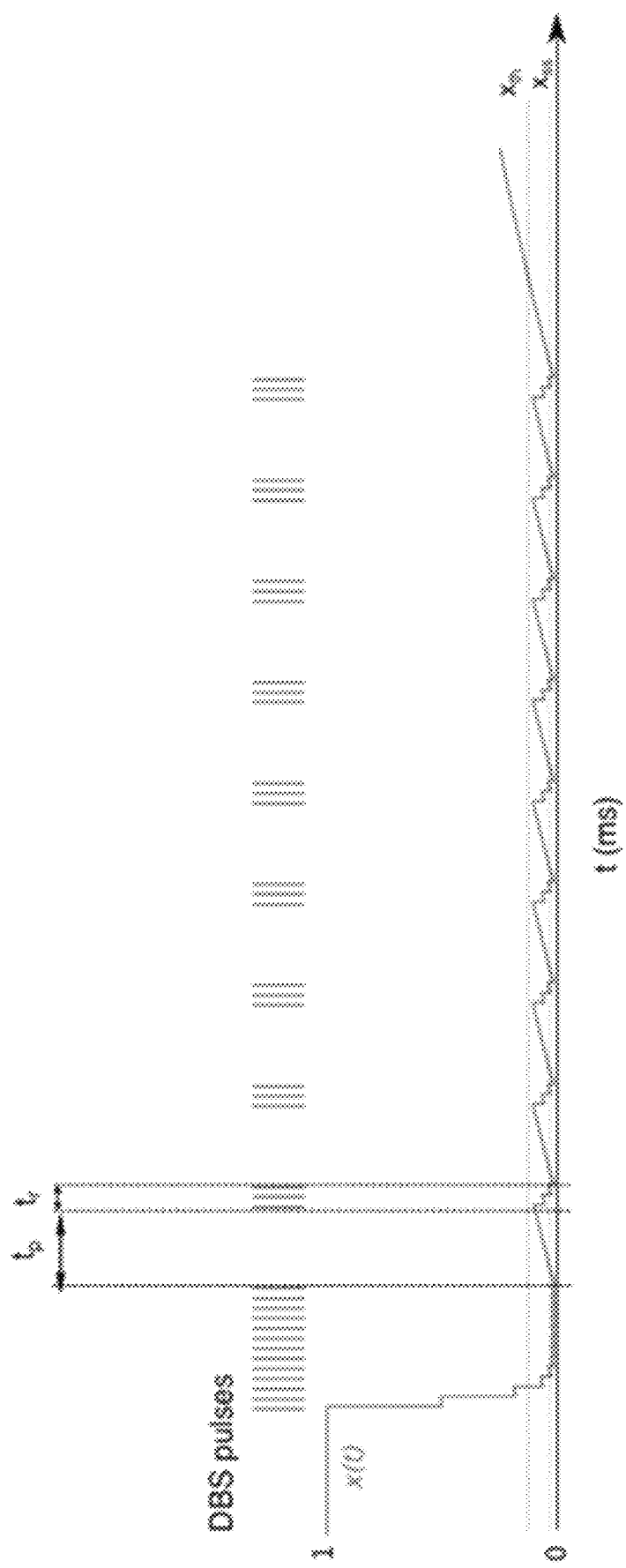
FIG. 9 illustrates a DBS pulsing strategy optimized to minimize the fraction of neurotransmitter resources that remain available after synaptic transmission, in connection with various aspects discussed herein.

Analytical details of DBS pulsing optimization can be based on the minimization of the parameter x (which yields maximization of u) in the TM equations (Equation (2)). Referring to FIG. 9, illustrated is a DBS pulsing strategy optimized to minimize the fraction of neurotransmitter resources that remain available after synaptic transmission, in connection with various aspects discussed herein. In FIG. 9, $t_p$ is the pause time, wherein there is no DBS pulsing, and $t_r$ is the run time, with DBS pulsing (the ratio $t_r/(t_r+t_p)$ gives the duty cycle). In the DBS pulsing strategy of FIG. 9, after the initial burst of DBS pulses (e.g., ~20, etc.), the solution for x reaches the steady state ($x_{ss}$). The DBS pulsing strategy of FIG. 9 is designed to keep the value of x between $x_{ss}$ and a certain threshold value ($x_{th}$). $x_{th}$ can be set as a fixed value so that it results in a desired change in the total firing rate of the model neuron. For example, as in the example of FIG. 9, it can be set to a percentage of the maximum value of x (e.g., a value between 1-10%, or lower or higher, etc.). Examples are provided below wherein setting $x_{th}$ with two different values can enable designs for tonic and bursting stimulation patterns.

Determination of DBS Run and Pause Times for a TM Synapse

The time lapse of x from the steady state ($x_{ss}$) to the threshold ($x_{th}$) represents the time period for pausing DBS pulsing, $t_p$ (pause time). Once $x=x_{th}$ pulsing can start again for a time of $t_r$ (run time) such that x returns to $x_{ss}$, and the cycle can repeat for the duration of DBS activity.

To find $t_p$, equation (2) can be solved for $t=(t_s, t_{s+1})$, where s is the number of the pulse, as shown in equations (6)-(8):

$$\frac{dx}{dt} = \frac{1-x}{\tau_d} \quad (6)$$

$$\int_{x_{ss}}^{x_{th}} \frac{dx}{1-x} = \int_{t_0}^{t'} \frac{dt}{\tau_d} \quad (7)$$

$$t' - t_0 = t_p = -\tau_d \ln\left(\frac{1-x_{th}}{1-x_{ss}}\right) \quad (8)$$

The discrete solutions of x and u can be used to find the run time for a synapse, by finding the values of x and u corresponding to each pulse, s. The next value of x at an incoming pulse $t_s$ is equal to equation (9):

$$x_{s+1} = x_s(1-u_{s+1})\exp\left(\frac{-\Delta t}{\tau_d}\right) + 1 - \exp\left(\frac{-\Delta t}{\tau_d}\right) \quad (9)$$

where $u_{s+1}$ is given by equation (10):

$$u_{s+1} = u_s\exp\left(\frac{-\Delta t}{\tau_f}\right) + U\left(1 - u_s\exp\left(\frac{-\Delta t}{\tau_f}\right)\right) \quad (10)$$

and $\Delta t$ is the time difference between two successive incoming pulses, as $$T_{dbs} = \frac{1}{f_{dbs}}.$$

The total decrease in x during running time of DBS, $t_r$, can be found, which is equal to some number of pulses, n, multiplied by the change in the value of x, called $\Delta x$, as shown in equation (12):

$$x_{th} - x_{ss} = n \cdot \Delta x \quad (12)$$

Hence, n can be found and multiplied by $T_{dbs}$ to find $t_r$. In other words, $t_r = n \cdot T_{dbs}$. Rewriting equation (9) for two successive incoming signals gives equations (13) and (14):

$$x_{n+2} = x_{n+1}(1-u_{n+2})\exp\left(\frac{-T_{dbs}}{\tau_d}\right) + 1 - \exp\left(\frac{-T_{dbs}}{\tau_d}\right) \quad (13)$$

$$x_{n+1} = x_n(1-u_{n+1})\exp\left(\frac{-T_{dbs}}{\tau_d}\right) + 1 - \exp\left(\frac{-T_{dbs}}{\tau_d}\right) \quad (14)$$

and subtracting them yields equation (15):

$$\Delta x = x_{n+2} - x_{n+1} = (x_{n+1}(1-u_{n+2}) - x_n(1-u_{n+1}))\exp\left(\frac{-T_{dbs}}{\tau_d}\right) \quad (15)$$

By substituting $\Delta x$ in equation (12) and solving for n, $t_r$ can be found by $t_r = n \cdot T_{dbs}$, which gives the run time solution.

In summary, after the initial burst of DBS pulses (e.g., ~20, etc.) until $x_{ss}$ is reached, the pulsing can be paused for a time equal to $t_p$ that is governed by equation (16):

$$t_p = -\tau_d \ln\left(\frac{1-x_{th}}{1-x_{ss}}\right) \quad (16)$$

and activated again for a running time given by equation (17):

$$t_r = \frac{(x_{th} - x_{ss})T_{dbs}}{(x_{n+1}(1-u_{n+2}) - x_n(1-u_{n+1}))\exp\left(-\frac{T_{dbs}}{\tau_d}\right)}, \quad (17)$$

or in terms of DBS frequency ($f_{dbs}$), by equation (18):

$$t_r = \frac{(x_{th} - x_{ss})}{(x_{n+1}(1-u_{n+2}) - x_n(1-u_{n+1}))} \cdot \frac{\sqrt[\tau_d \cdot f_{dbs}]{e}}{f_{dbs}} \quad (18)$$

Note that the values for $x_{th}$ and $x_{ss}$ are much less than 1, which results in a Taylor expansion around x=0 as: $t_p \sim \tau_d \cdot x_{th}$ for each synapse. The exact values of $t_p$ are 11, 68 and 33 ms for F, D and P synapses, respectively, when $x_{th}$ is set to 10% of the maximum value of x ($x_{th}=0.1$). Obviously $t_r$ depends on the DBS frequency and the type of synapse and is controlled by the discrete values of x and u. Note that decreasing the threshold value ($x_{th}$) leads to less run time ($t_r$), which in turn leads to tonic pulsing instead of bursts of pulses.

Determination of Run and Pause Times for Population of TM Synapses

The synaptic populations do not necessarily contain a single synapse type (F, D or P). Instead, they are usually composed of a distribution of these synapse types. Therefore, the method can be generalized to minimization of x across the various synapse types. In this manner, different values of $t_r$ and $t_p$ can be generated following the weighted sum of their individual values for each synapse, as in equation (19):

$$t_{r,p_{av}} = \frac{\sum_{i=1}^{3} w_i t_{r,p_i}}{\sum_{i=1}^{3} w_i} \quad (19)$$

where i=1, 2 and 3 corresponds to F, D and P synapses respectively. $w_i$ denotes the population percentage of each synapse type. Note that $t_r$ and $t_p$ for each synapse can be calculated by equations (16) and (18).

The Difference Between Tonic and Burst Stimulation Optimization

For optimized stimulation, the difference between two different pulsing methods of 810 and 820 arises from the initial setting of the threshold value $x_{th}$. For one example threshold, setting $x_{th}$=0.035 (a very low threshold, close to zero) leads to tonic stimulation as in example 810. Solving equations (16) and (18) and substituting them into equation (19) can give $t_p$ and $t_r$ for a population of different synapse types. In such a scenario, $t_r$ is so low that it ends up with tonic pulsing after reaching the steady state ($t_r$ is not long enough to contain more than one pulse). However, for another example threshold, setting $x_{th}$=0.1 (10% of the maximum value of x) leads to bursts of DBS after the initial signaling period, as in example 820. Solving for $t_r$ an $t_p$ in such a scenario leads to a run time that is long enough to contain a number of pulses of DBS (a burst).

6. Discussion

The example use case developed a simple model system that is capable of capturing the general features of DBS-induced synaptic suppression. That model was then used to demonstrate the relevance of synaptic suppression when analyzing experimental recordings of DBS peri-stimulus time histograms. Finally, the model was inverted to identify alternative DBS pulsing strategies that maximize the degree of synaptic suppression with the minimum number of stimuli. The theoretical results of the example use case represent a step toward dissecting the effects of DBS from the perspective of synaptic first principles. Extrapolation to analyses on network level effects can begin based on an understanding of the effects of DBS at the level of the synapse. The contrasting approach of ignoring the basics of DBS-induced synaptic dynamics while attempting to perform network activity analyses is unlikely to be a sound strategy.

The example use case hypothesized that the fundamental goal of brain stimulation therapies is to use the electrical pulses to control the release of neurotransmitters in targeted brain circuits. Tenets of this hypothesis are that low frequency stimulation can be used to facilitate neurotransmitter release in directly activated pathways, while high frequency stimulation can suppress synaptic communication via the mechanisms described in this study. In vitro electrophysiology studies support the general concepts of DBS-induced synaptic suppression. In addition, recent computational studies and intraoperative human recordings have demonstrated the relevance of synaptic suppression in understanding and interpreting the neural activity patterns recorded during DBS. The results of the example use case predict an optimal (minimal) tonic stimulation frequency of 95 Hz for maintaining glutamatergic synaptic suppression, as in example 810. In line with that finding, blinded clinical trials have not been able to show a statistically significant therapeutic difference after the DBS frequency exceeds 100 Hz. As such, it appears that explicit representation of DBS-induced synaptic dynamics is likely to be a key factor in developing physiologically accurate models of the network activity generated by DBS.

Computational models designed to study the network activity generated by DBS have historically ignored the role of synaptic suppression, and synaptic plasticity in general, in their analyses. Instead, DBS network models have tended to focus on the interplay between static excitatory and inhibitory synaptic conductances in the generation of rhythmic bursting activity, and the subsequent disruption of that bursting activity with DBS. These models achieve burst disruption by overriding the underlying neural spiking and replacing it with high frequency activity that is permeated throughout the network. However, experimental recordings of DBS-induced neural activity do not coincide with these kinds of network model predictions, as seen in FIGS. 3, 6, and 7. Alternatively, the concepts of DBS-induced synaptic suppression suggest that the primary network effects of high frequency DBS is to reduce or minimize the influence from directly stimulated pathways on the overall network activity patterns.

Common physiological features that regulate synaptic modulation may converge around the theme of short bursts of pre-synaptic activity. However, these various features likely occur on different time scales. Synaptic suppression is an acute effect that occurs on a short time scale (seconds). Spike timing dependent plasticity is a longer lasting effect that occurs on a medium time scale (minutes). Then there are also intrinsic homeostatic control mechanisms regulating synaptic connections that act over a long time scale (hours). Therefore, it appears that the future of DBS network modeling may involve an explicit integration of these kinds of synaptic modulation features into the simulations.

The example use case employed a simple phenomenological model of synaptic dynamics, albeit explicitly parameterized to match glutamatergic synapses in cortex. Various embodiments can extend this synapse model in additional ways to better optimize DBS stimulation. For example, some embodiments can employ DBS stimulation further optimized based on a model accounting at least partly for the multiple pools of synaptic vesicles. Detailed analyses of synaptic vesicles suggest there is a readily releasable pool, readily priming pool, premature pool, and resting pool. Under high frequency stimulation conditions, the depletion and replenishment of these various pools can be difficult to estimate, and high frequency stimulation has been shown to enhance the rate of replenishment. Unfortunately, the details of replenishment during long-term high frequency stimulation are currently undocumented. This gap in knowledge represents an important opportunity for collaboration between the basic science of synaptic physiology and the clinical application of DBS technology.

DBS research is currently benefiting from large initiatives, sponsored by both government and industry, which focus on understanding the brain network connections and neural activity patterns that underlie disease states, as well as their modulation by stimulation. In addition to embodiments discussed herein, another contribution of the example use case to that larger body of work is an alternative perspective that many of the network level responses generated by DBS may be rooted in the biophysics of the individual synapses that are being driven by DBS. It appears that exploiting the physiological limits of the synaptic machinery to suppress connectivity is a basic mechanism of DBS and a simple model of those processes can be used to optimize DBS pulsing at the level of the synapse. These basic concepts can then be customized within larger network models that explicitly account for the neural connectivity and activity patterns that are representative of the disease state being studied.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with method 100 or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Figure 10:
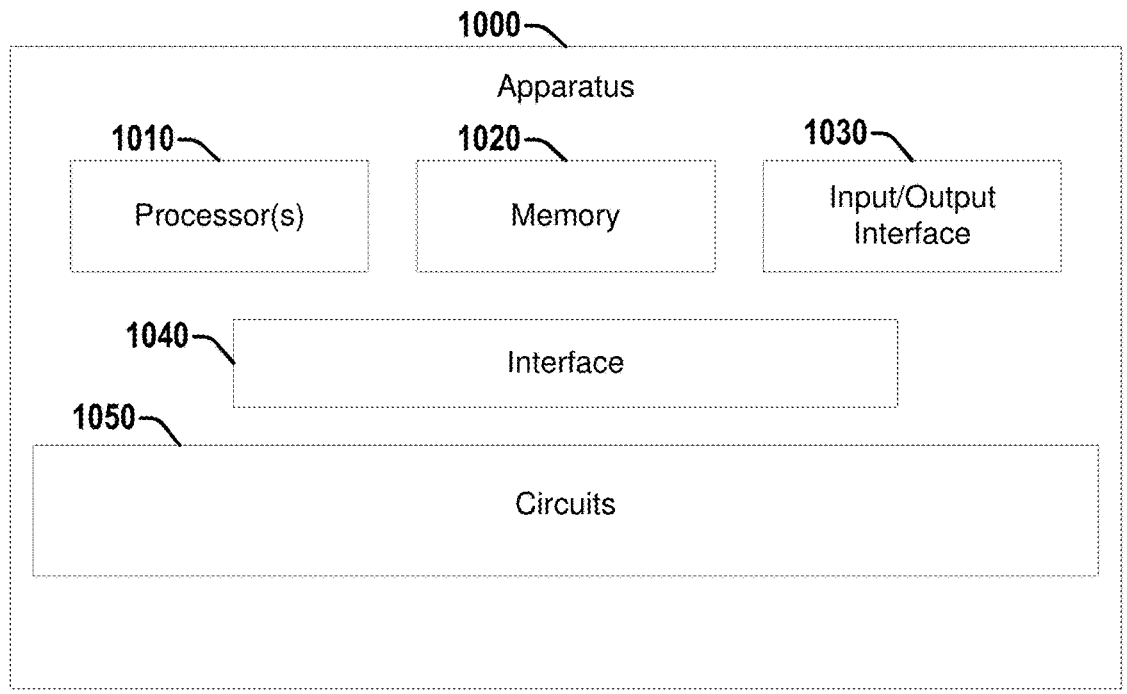
FIG. 10 illustrates a diagram of an example apparatus that can DBS pulsing strategies that maximize synaptic suppression with the minimum number of stimuli and/or facilitate configuration of a DBS system to implement such DBS pulsing strategies.

Referring to FIG. 10, illustrated is a diagram of an example apparatus 1000 that can facilitate DBS pulsing strategies that maximize synaptic suppression with the minimum number of stimuli and/or facilitate configuration of a DBS system to implement such DBS pulsing strategies, according to various embodiments discussed herein. Apparatus 1000 can be configured to perform various techniques discussed herein, for example, various operations discussed in connection with sets of operations 200. Apparatus 1000 can comprise one or more processors 1010 and memory 1020. Processor(s) 1010 can, in various embodiments, comprise circuitry such as, but not limited to, one or more single-core or multi-core processors. Processor(s) 1010 can include any combination of general-purpose processors and dedicated processors (e.g., graphics processors, application processors, etc.). The processor(s) can be coupled with and/or can comprise memory (e.g., of memory 1020) or storage and can be configured to execute instructions stored in the memory 1020 or storage to enable various apparatus, applications, or operating systems to perform operations and/or methods discussed herein. Memory 1020 can be configured to store one or more DBS pulsing patterns or strategies.

Apparatus 1000 can also comprise an input/output (I/O) interface 1030 (e.g., associated with one or more I/O devices), a set of circuits 1050, and an interface 1040 that connects the processor(s) 1010, the memory 1020, the I/O interface 1030, and the set of circuits 1050. I/O interface 1030 can be configured to transfer data between memory 1020, processor 1010, circuits 1050, and external devices, for example, a DBS system (e.g., DBS system 100).

The processor(s) 1010 and/or one or more circuits of the set of circuits 1050 can perform one or more acts associated with a method or set of operations discussed herein, such as set of operations 200 and/or configure a DBS system to perform such a method or set of operations. In various embodiments, different acts (e.g., different operations of a set of operations) can be performed by the same or different processor(s) 1010 and/or one or more circuits of the set of circuits 1050.

Examples herein can include subject matter such as an apparatus, a DBS system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to implement one or more DBS pulsing strategies that maximize synaptic suppression with the minimum number of stimuli and/or configure a DBS system to implement such, according to embodiments and examples described.

Example 1 is a non-transitory computer-readable medium storing computer-executable instructions that, when executed, cause a processor to perform operations, comprising: applying deep brain stimulation (DBS) electrical stimulation according to a first mode to cause steady-state excitatory post-synaptic current (EPSC) suppression in a set of synapses; and applying DBS electrical stimulation according to a second mode that is different than the first mode to maintain EPSC suppression in the set of synapses.

Example 2 comprises the subject matter of any variation of any of example(s) 1, wherein applying DBS electrical stimulation according to the first mode comprises applying a plurality of high frequency pulses.

Example 3 comprises the subject matter of any variation of any of example(s) 2, wherein the plurality of high frequency pulses have a frequency of around 130 Hz.

Example 4 comprises the subject matter of any variation of any of example(s) 1-3, wherein applying DBS electrical stimulation according to the second mode comprises applying tonic stimuli at a lower frequency than a frequency of the first mode.

Example 5 comprises the subject matter of any variation of any of example(s) 4, wherein the lower frequency is around 95 Hz.

Example 6 comprises the subject matter of any variation of any of example(s) 1-5, wherein applying DBS electrical stimulation according to the second mode comprises applying pulses at a frequency of the first mode according to a reduced duty cycle.

Example 7 comprises the subject matter of any variation of any of example(s) 6, wherein applying pulses at the frequency of the first mode according to the reduced duty cycle comprises repeatedly alternating between applying the pulses during a run time and inactivity during a pause time.

Example 8 comprises the subject matter of any variation of any of example(s) 1-7, wherein maintaining EPSC suppression in the set of synapses comprises maintaining a fraction of neurotransmitter resources that remain available after synaptic transmission below a threshold value for the fraction of neurotransmitter resources that remain available after synaptic transmission.

Example 9 comprises the subject matter of any variation of any of example(s) 8, wherein the threshold value for the fraction of neurotransmitter resources that remain available after synaptic transmission is less than or equal to 10%.

Example 10 is a deep brain stimulation (DBS) system, comprising: a neurostimulator configured to generate DBS electrical stimulation, wherein the DBS electrical stimulation comprises: generating deep brain stimulation (DBS) electrical stimulation according to a first mode to cause steady-state excitatory post-synaptic current (EPSC) suppression in a set of synapses; and generating DBS electrical stimulation according to a second mode that is different than the first mode to maintain EPSC suppression in the set of synapses; and a lead configured to apply the DBS electrical stimulation to the set of synapses.

Example 11 comprises the subject matter of any variation of any of example(s) 10, wherein generating DBS electrical stimulation according to the first mode comprises generating a plurality of high frequency pulses.

Example 12 comprises the subject matter of any variation of any of example(s) 11, wherein the plurality of high frequency pulses have a frequency of around 130 Hz.

Example 13 comprises the subject matter of any variation of any of example(s) 10-12, wherein generating DBS electrical stimulation according to the second mode comprises generating tonic stimuli at a lower frequency than a frequency of the first mode.

Example 14 comprises the subject matter of any variation of any of example(s) 13, wherein the lower frequency is around 95 Hz.

Example 15 comprises the subject matter of any variation of any of example(s) 10-14, wherein generating DBS electrical stimulation according to the second mode comprises generating pulses at a frequency of the first mode according to a reduced duty cycle.

Example 16 comprises the subject matter of any variation of any of example(s) 15, wherein generating pulses at the frequency of the first mode according to the reduced duty cycle comprises repeatedly alternating between generating the pulses during a run time and inactivity during a pause time.

Example 17 comprises the subject matter of any variation of any of example(s) 10-16, wherein maintaining EPSC suppression in the set of synapses comprises maintaining a fraction of neurotransmitter resources that remain available after synaptic transmission below a threshold value for the fraction of neurotransmitter resources that remain available after synaptic transmission.

Example 18 comprises the subject matter of any variation of any of example(s) 17, wherein the threshold value for the fraction of neurotransmitter resources that remain available after synaptic transmission is less than or equal to 10%.

Example 19 is a method, comprising: applying deep brain stimulation (DBS) electrical stimulation according to a first mode to cause steady-state excitatory post-synaptic current (EPSC) suppression in a set of synapses; and applying DBS electrical stimulation according to a second mode that is different than the first mode to maintain EPSC suppression in the set of synapses.

Example 20 comprises the subject matter of any variation of any of example(s) 19, wherein applying DBS electrical stimulation according to the first mode comprises applying a plurality of high frequency pulses.

Example 21 comprises the subject matter of any variation of any of example(s) 20, wherein the plurality of high frequency pulses have a frequency of around 130 Hz.

Example 22 comprises the subject matter of any variation of any of example(s) 19-21, wherein applying DBS electrical stimulation according to the second mode comprises applying tonic stimuli at a lower frequency than a frequency of the first mode.

Example 23 comprises the subject matter of any variation of any of example(s) 22, wherein the lower frequency is around 95 Hz.

Example 24 comprises the subject matter of any variation of any of example(s) 19-23, wherein applying DBS electrical stimulation according to the second mode comprises applying pulses at a frequency of the first mode according to a reduced duty cycle.

Example 25 comprises the subject matter of any variation of any of example(s) 24, wherein applying pulses at the frequency of the first mode according to the reduced duty cycle comprises repeatedly alternating between applying the pulses during a run time and inactivity during a pause time.

Example 26 comprises the subject matter of any variation of any of example(s) 19-25, wherein maintaining EPSC suppression in the set of synapses comprises maintaining a fraction of neurotransmitter resources that remain available after synaptic transmission below a threshold value for the fraction of neurotransmitter resources that remain available after synaptic transmission.

Example 27 comprises the subject matter of any variation of any of example(s) 26, wherein the threshold value for the fraction of neurotransmitter resources that remain available after synaptic transmission is less than or equal to 10%.

Example 28 comprises an apparatus comprising means for executing any of the described operations of examples 1-27.

Example 29 comprises a machine readable medium that stores instructions for execution by a processor to perform any of the described operations of examples 1-27.

Example 30 comprises an apparatus comprising: a memory; and one or more processors configured to: perform any of the described operations of examples 1-27.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A deep brain stimulation (DBS) system, comprising:
   a neurostimulator configured to generate DBS electrical stimulation, wherein the DBS electrical stimulation comprises:
   generating deep brain stimulation (DBS) electrical stimulation according to a first mode to cause steady-state excitatory post-synaptic current (EPSC) suppression in a set of synapses, wherein while applying DBS electrical stimulation according to the first mode, an EPSC of the set of synapses is suppressed from having a first EPSC amplitude to having a second EPSC amplitude that is less than the first EPSC amplitude, and wherein generating the DBS electrical stimulation according to the first mode comprises applying a first number of pulses at a frequency over a period of time; and
   generating DBS electrical stimulation according to a second mode that is different than the first mode to maintain the steady-state EPSC suppression in the set of synapses, wherein while applying DBS electrical stimulation according to the second mode, the EPSC of the set of synapses changes from having the second EPSC amplitude to having a third EPSC amplitude that is greater than the second EPSC amplitude, wherein generating DBS electrical stimulation according to the second mode comprises applying a second number of pulses at the frequency over the period of time, and wherein the second number of pulses is less than the first number of pulses; and
   a lead configured to apply the DBS electrical stimulation to the set of synapses.

2. The DBS system of claim 1, wherein the frequency is above 100 hertz (Hz).

3. The DBS system of claim 1, wherein the first mode applies the frequency until a fraction of neurotransmitter resources that remain available after synaptic transmission reaches a steady state.

4. The DBS system of claim 1, wherein the frequency is 130 Hz.

5. The DBS system of claim 1, wherein the frequency is in a range of between 120 Hz and 140 Hz.

6. The DBS system of claim 1, wherein the second mode comprises operating at the frequency according to a reduced duty cycle comprising a repeating pattern of DBS pulses during a run time followed by inactivity during a pause time.

7. A non-transitory computer-readable medium storing computer-executable instructions that, when executed, cause a processor to perform operations, comprising:
   applying deep brain stimulation (DBS) electrical stimulation according to a first mode to cause steady-state excitatory post-synaptic current (EPSC) suppression in a set of synapses, wherein while applying DBS electrical stimulation according to the first mode, an EPSC of the set of synapses is suppressed from having a first EPSC amplitude to having a second EPSC amplitude that is less than the first EPSC amplitude, and wherein applying the DBS electrical stimulation according to the first mode comprises applying a first number of pulses at a frequency over a period of time; and
   applying DBS electrical stimulation according to a second mode that is different than the first mode to maintain the steady-state EPSC suppression in the set of synapses, wherein while applying DBS electrical stimulation according to the second mode, the EPSC of the set of synapses changes from having the second EPSC amplitude to having a third EPSC amplitude that is greater than the second EPSC amplitude, wherein applying DBS electrical stimulation according to the second mode comprises applying a second number of pulses at the frequency over the period of time, and wherein the second number of pulses is less than the first number of pulses.

8. The non-transitory computer-readable medium of claim 7, wherein:
   the first number of pulses comprises 20 pulses; and
   the second number of pulses comprises 4 pulses.

9. The non-transitory computer-readable medium of claim 8, wherein applying the DBS electrical stimulation according to the second mode comprises applying the second number of pulses at the frequency every 37 milliseconds over the period of time.

10. The non-transitory computer-readable medium of claim 9, wherein the frequency is 130 hertz (Hz).

11. The non-transitory computer-readable medium of claim 10, wherein maintaining the EPSC suppression in the set of synapses comprises maintaining a fraction of neurotransmitter resources that remain available after synaptic transmission below a threshold value for the fraction of neurotransmitter resources that remain available after synaptic transmission, and wherein the threshold value for the fraction of neurotransmitter resources that remain available after synaptic transmission is less than or equal to 10%.

12. The non-transitory computer-readable medium of claim 7, wherein the first mode applies the frequency of the first mode until a fraction of neurotransmitter resources that remain available after synaptic transmission reaches a steady state.

13. The non-transitory computer-readable medium of claim 7, wherein the set of synapses are in a brain of a patient.

14. A method, comprising:
applying deep brain stimulation (DBS) electrical stimulation according to a first mode to initiate steady-state excitatory post-synaptic current (EPSC) suppression in a set of synapses, wherein while applying DBS electrical stimulation according to the first mode, an EPSC of the set of synapses is suppressed from having a first EPSC amplitude to having a second EPSC amplitude that is less than the first EPSC amplitude;
applying DBS electrical stimulation according to a second mode that is different than the first mode to maintain the steady-state EPSC suppression in the set of synapses, wherein while applying DBS electrical stimulation according to the second mode, the EPSC of the set of synapses changes from having the second EPSC amplitude to having a third EPSC amplitude that is greater than the second EPSC amplitude; and
wherein applying DBS electrical stimulation according to the second mode comprises applying pulses at a frequency of the first mode according to a reduced duty cycle.

15. The method of claim 14, wherein the second mode includes bursts with 4 pulses at 130 Hz delivered every 37 ms.

16. The method of claim 15, wherein the frequency of the first mode is 130 Hz.

17. The method of claim 14, wherein the first mode applies the frequency of the first mode until a fraction of neurotransmitter resources that remain available after synaptic transmission reaches a steady state.

18. The method of claim 17, wherein the set of synapses are in a brain of a patient.

19. The method of claim 14, wherein applying pulses at the frequency of the first mode according to the reduced duty cycle comprises repeatedly alternating between applying the pulses during a run time and inactivity during a pause time.

20. The method of claim 14, wherein maintaining the steady-state EPSC suppression in the set of synapses comprises maintaining a fraction of neurotransmitter resources that remain available after synaptic transmission below a threshold value for the fraction of neurotransmitter resources that remain available after synaptic transmission.

21. The method of claim 20, wherein the threshold value for the fraction of neurotransmitter resources that remain available after synaptic transmission is less than or equal to 10%.

22. The method of claim 14, wherein:
applying the DBS electrical stimulation according to the first mode comprises applying a first number of pulses at the frequency of the first mode over a period of time; and
applying DBS electrical stimulation according to the second mode comprises applying a second number of pulses at the frequency of the first mode over the period of time, wherein the second number of pulses is less than the first number of pulses.

23. The method of claim 22, wherein applying DBS electrical stimulation according to the second mode comprises applying the second number of pulses at the frequency of the first mode a first time during a first portion of the period of time, comprises a pulse-free period during a second portion of the period of time, and comprises applying the second number of pulses at the frequency of the first mode a second time during a third portion of the period of time, wherein the second portion of the period of time occurs between the first portion of the period of time and the third portion of the period of time.

24. The method of claim 23, wherein:
the set of synapses comprises one or more depressing synapses, one or more facilitating synapses, and one or more pseudo-linear synapses; and
the second portion of the period of time is based on a weighted sum of calculated pause times for the one or more depressing synapses, the one or more facilitating synapses, and the one or more pseudo-linear synapses.

25. The method of claim 24, wherein the set of synapses are glutamatergic synapses.

26. The method of claim 22, wherein applying DBS electrical stimulation according to the second mode comprises applying the second number of pulses at the frequency of the first mode over a run time that is less than the period of time.

27. The method of claim 14, wherein:
the steady-state EPSC suppression occurs in the set of synapses when the EPSC of the set of synapses has an EPSC amplitude that is less than or equal to a steady-state EPSC amplitude;
the first EPSC amplitude is greater than the steady-state EPSC amplitude;
the second EPSC amplitude is less than the steady-state EPSC amplitude; and
the third EPSC amplitude is less than or equal to the steady-state EPSC amplitude.

* * * * *